United States Patent [19]

Connor et al.

[11] 4,382,939

[45] May 10, 1983

[54] 3-[2-(MONO-AND DIALKYLAMINO)PROPYL]-1,2,3,4-TETRAHYDRO-5H-[1]BENZOPYRANO[3,4-C]PYRIDIN-5-ONES USEFUL FOR TREATING BRONCHOSPASTIC DISEASES

[75] Inventors: David T. Connor, Ann Arbor; Charles F. Schwender, Dexter; Roderick J. Sorenson; Paul C. Unangst, both of Ann Arbor, all of Mich.

[73] Assignee: Warner Lambert Company, Morris Plains, N.J.

[21] Appl. No.: 351,554

[22] Filed: Feb. 23, 1982

[51] Int. Cl.$^3$ ............... A61K 31/455; C07D 491/052
[52] U.S. Cl. .................................. 424/256; 546/62; 546/65; 546/89; 546/92
[58] Field of Search ............... 546/62, 65, 89, 92; 424/256

[56] References Cited

U.S. PATENT DOCUMENTS 4,276,296  6/1981  Brown et al. .................. 424/256

OTHER PUBLICATIONS

Modern Synthetic Reactions, House, W. A. Benjamin, New York, p. 16 (1965).
Fieser et al., Advanced Organic Chem., Reinhold Publishing Co., p. 496–497 (1961).

*Primary Examiner*—John M. Ford
*Assistant Examiner*—Bernard Dentz
*Attorney, Agent, or Firm*—Ronald A. Daignault

[57] ABSTRACT

Anticholinergic 3-[2-(mono- and dialkylamino)-propyl]-1,2,3,4-tetrahydro-5$\underline{H}$-[1]benzopyrano[3,4-c]-pyridin-5-ones useful for treating bronchospastic diseases in mammals are disclosed. Also disclosed are methods for preparing said compounds, pharmaceutical compositions containing them and methods for using said pharmaceutical compositions.

A method for preparing the intermediate which is required to prepare the unsubstituted benzopyrano-[3,4-c]pyridin-5-ones of the invention is also disclosed.

15 Claims, No Drawings

3-[2-(MONO-AND DIALKYLAMINO)PROPYL]-1,2,3,4-TETRAHYDRO-5H-[1]BENZOPYRANO[3,4-C]PYRIDIN-5-ONES USEFUL FOR TREATING BRONCHOSPASTIC DISEASES

BACKGROUND OF THE INVENTION

The compounds of the invention are 3-[2-(mono-and dialkylamino)propyl]-1,2,3,4-tetrahydro-5H-[1]benzopyrano[3,4-c]pyridin-5-ones which have anticholinergic activity. The compounds are useful as bronchodilators.

U.S. Pat. No. 4,276,296 discloses anticholinergic 3-[2-(1-pyrrolidinyl and 1-piperidinyl)propyl]-1,2,3,4-tetrahydro-5H-[1]benzopyrano[3,4-c]pyridin-5-ones.

SUMMARY OF THE INVENTION

The invention sought to be patented in its generic chemical compound aspect is a compound having the structural formula I

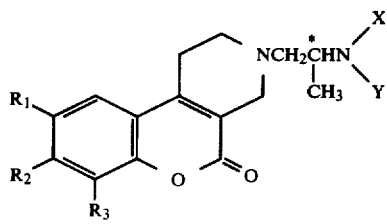

*indicates an asymmetric carbon atom.

wherein
  $R_1$ is H, alkyl of from 1 to 6 carbon atoms, alkoxy of from 1 to 6 carbon atoms, halo, or acetylamino;
  $R_2$ is H, alkyl of from 1 to 6 carbon atoms, or alkoxy of from 1 to 6 carbon atoms;
  $R_3$ is H, or alkoxy of from 1 to 6 carbon atoms;
  $R_1$ and $R_2$ taken together are $OCH_2O$;
  $R_2$ and $R_3$ taken together are $CH=CH-CH=CH$;
  X is $CH_3$, $C_2H_5$, n-$C_3H_7$, or n-$C_4H_9$;
  Y is H, $CH_3$, $C_2H_5$ n-$C_3H_7$, n-$C_4H_9$, or s-$C_4H_9$;
and the pharmaceutically acceptable salts thereof, provided that $R_1$ and $R_2$ are not both $OCH_3$ when Y is H.

The invention sought to be patented in a first subgeneric chemical compound aspect is a compound having structural formula I wherein $R_3$ is H; and the pharmaceutically acceptable salts thereof.

The invention sought to be patented in a second subgeneric chemical compound aspect is a compound having structural formula I wherein $R_3$ is H, X is $C_3$ or $C_2H_5$; and the pharmaceutically acceptable salts thereof.

The invention sought to be patented in a first specific chemical compound aspect is the compound having the name 3-[2-(dimethylamino)propyl]-1,2,3,4-tetrahydro-8,9-dimethoxy-5H-[1]benzopyrano[3,4-c]pyridin-5-one and the pharmaceutically acceptable salts thereof.

The invention sought to be patented in a second specified chemical compound aspect is the compound having the name 3-[2-(ethylamino)propyl]-1,2,3,4-tetrahydro-5H-[1]benzopyrano[3,4-c]pyridin-5-one and the pharmaceutically acceptable salts thereof.

The invention sought to be patented in a third specific chemical compound aspect is the compound having the name 3-[2-(dimethylamino)propyl]-1,2,3,4-tetrahydro-8,9-diethoxy-5H-[1]benzopyrano[3,4-c]pyridin-5-one and the pharmaceutically acceptable salts thereof.

The invention sought to be patented in a fourth specific chemical compound aspect is the compound having the name 3-[2-(dimethylamino)propyl]-1,2,3,4-tetrahydro-8-methyl-5H-[1]benzopyrano[3,4-c]pyridin-5-one and the pharmaceutically acceptable salts thereof.

The invention sought to be patented in a fifth specific chemical compound aspect is the compound having the name 3-[2-(dimethylamino)propyl]-1,2,3,4-tetrahydro-5H-[1]benzopyrano[3,4-c]pyridin-5-one and the pharmaceutically acceptable salts thereof.

The invention sought to be patented in a sixth specific chemical compound aspect is the compound having the name 3-[2-(ethylamino)propyl]-1,2,3,4-tetrahydro-8-methoxy-5H-[1]benzopyrano[3,4-c]pyridin-5-one and the pharmaceutically acceptable salts thereof.

The invention sought to be patented in a seventh specific chemical compound aspect is the compound having the name 3-[2-(ethylmethylamino)propyl]-1,2,3,4-tetrahydro-8-methyl-5H-[1]benzopyrano[3,4-c]pyridin-5-one and the pharmaceutically acceptable salts thereof.

The invention sought to be patented in an eighth specific chemical compound aspect is the compound having the name 3-[2-(diethylamino)propyl]-1,2,3,4-tetrahydro-8-methyl-5H-[1]benzopyrano[3,4-c]pyridin-5-one and the pharmaceutically acceptable salts thereof.

The invention sought to be patented in a ninth specific chemical compound aspect is the compound having the name 3-[2-(diethylamino)propyl]-1,2,3,4-tetrahydro-5H-[1]benzopyrano[3,4-c]pyridin-5-one and the pharmaceutically acceptable salts thereof.

The invention sought to be patented in a tenth specific chemical compound aspect is the compound having the name 3-[2-(diethylamino)propyl]-1,2,3,4-tetrahydro-8,9-dimethoxy-5H-[1]benzopyrano[3,4-c]pyridin-5-one and the pharmaceutically acceptable salts thereof.

The invention sought to be patented in its first generic chemical process aspect is a process for preparing a chemical compound having structural formula I which comprises reacting a compound having structural formula II with an amine having the formula $H_2NX$ to produce a compound having the structural formula III and if desired, N-alkylating the so produced compound having formula III.

The invention sought to be patented in its second generic chemical process aspect is a process for preparing a chemical compound having structural formula IV' which comprises contacting a compound having structural formula VIII with elemental hydrogen.

The invention sought to be patented in its pharmaceutical composition aspect is a composition consisting essentially of a compound having structural formula I in combination with a pharmaceutically acceptable carrier.

The invention sought to be patented in its pharmaceutical method aspect is a method for treating asthma or bronchitis in a mammal in need of such treatment, which comprises administering an effective amount of the above defined pharmaceutical composition to said mammal.

DESCRIPTION OF THE PREFERRED EMBODIMENTS

The compounds of the invention having structural formula I

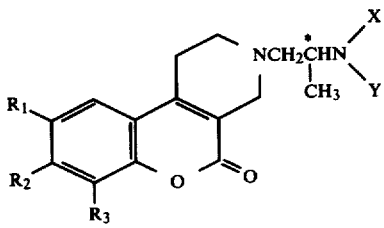

wherein $R_1$, $R_2$, $R_3$, X and Y are defined above may be prepared by different procedures which are considered equivalent for purposes of the invention. One such procedure involves the reaction of a compound of structural formula II with a primary amine of the formula

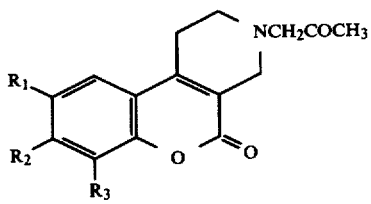

$H_2NX$ under reducing conditions to produce a compound having structural formula III.

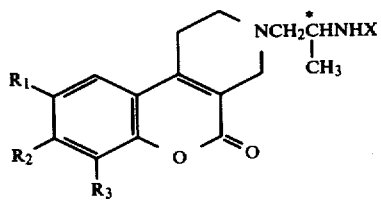

This reaction proceeds most conveniently by first contacting compound II and the amine in a convenient solvent in the presence of a dehydrating agent, such as anhydrous calcium sulfate, to produce the corresponding imine. The so produced imine is isolated and treated with $H_2$ and a suitable catalyst such as Pt/C to produce compound III.

The compounds of formula III are themselves compounds of the invention (i.e. compounds of formula I wherein Y is H) and may be converted into additional compounds of the invention having structural formula I wherein X is defined above and Y is $CH_3$, $C_2H_5$, n-$C_3H_7$, n-$C_4H_9$, or s-$C_4H_9$ by known procedures. For example, a compound of formula III may be methylated by treatment with formaldehyde in the presence of a reducing agent such as sodium borohydride. Other alkylation procedures such as treatment with an alkanoic acid, $ZCO_2H$ (wherein Z is an alkyl group containing one less carbon atom than the desired alkyl group being added) in the presence of sodium borohydride are also contemplated. Compounds of structural formula I wherein X and Y are both $CH_3$ may also be conveniently prepared directly from compound II by treatment with $(CH_3)_2NH$ under reducing conditions, e.g. $H_2$, Pd/C. Additional alkylation procedures will be familiar to those skilled in the art, and are contemplated by the invention.

The compounds of structural formula II may be prepared from a compound having structural formula IV

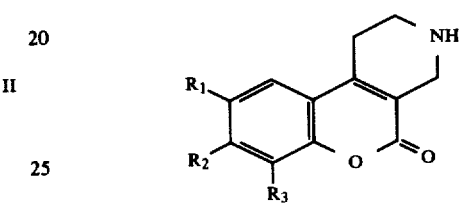

by treatment with a 1-halo-2-propanone, 1-chloro-2-propanone is preferred. This reaction proceeds conveniently in a nonreactive solvent such as methanol, preferably at reflux temperature, in the presence of an acid acceptor such as a tertiary amine, e.g. triethylamine.

The requisite compounds of structural formula IV are prepared by condensing a properly substituted phenol having structural formula V with 4-oxo-3-piperidine-carboxylic acid, VI.

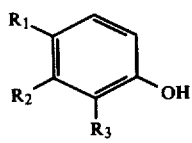

This condensation is conveniently performed in concentrated sulfuric acid (preferably about 75% $H_2SO_4$) utilizing VI in the form of its methyl ester, hydrochloride, which is commercially available (e.g. from Aldrich Chemical Co., Milwaukee, WI 53201, U.S.A.). The phenols of structural formula V are either commercially available or may be prepared by conventional procedures known to those skilled in the art.

The intermediate of structural formula IV wherein $R_1=R_2=R_3=H$ (IV') is disclosed in British Pat. No. 1,455,522 example 2. The synthetic method described therein reports a 10% yield, but could not be consistently reproduced. This compound was successfully prepared according to the following reaction sequence.

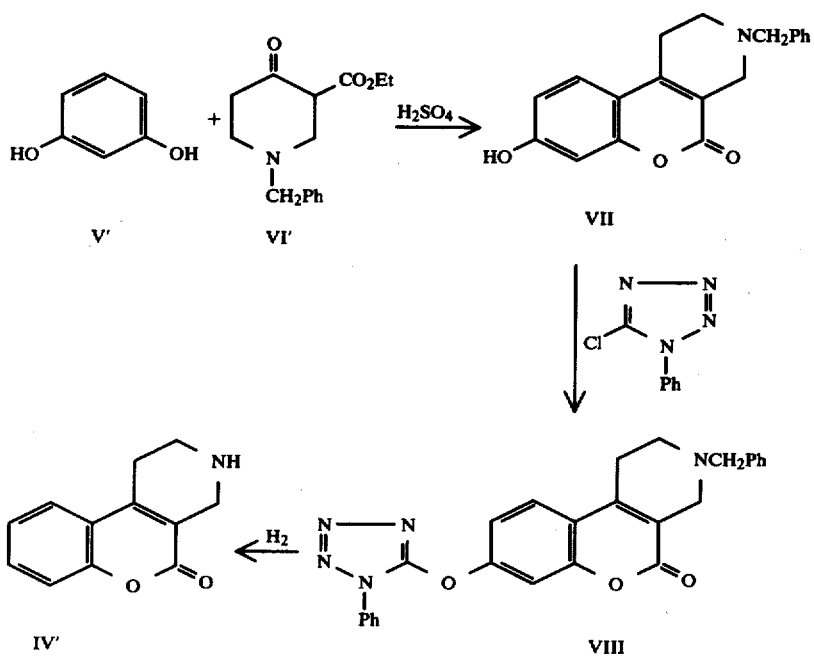

The condensation between resorcinol (V') and 1-benzyl-3-carbethoxy-4-piperidone (VI') to produce compound VII is carried out in substantially the same manner as the condensation between compounds V and VI described above. The compound VI' may be prepared as described in Beilstein 22 (2) 216. Those skilled in the art will recognize that other carbalkoxy groups may be present at the 3-position of VI' and that the same product VII will thereby be produced. Carbethoxy is preferred. The reaction between VII and 5-chloro-1-phenyl-1H-tetrazole [Beilstein, 26, (2), 197] is carried out in a convenient non-reactive solvent such as dimethylformamide or dimethylsulfoxide in the presence of an acid acceptor such as sodium carbonate, potassium carbonate, and the like. This reaction proceeds efficiently at a temperature of about 70°–100° C. and is substantially complete in about 3 to about 10 hours. Compound VIII is converted to IV' by reaction with elemental hydrogen using standard procedures. For example, the reaction proceeds efficiently at room temperature in acetic acid at about 50 lbs/in² hydrogen pressure in the presence of 20% Pd/C. The reaction is complete when hydrogen uptake ceases. Other hydrogenation procedures are considered equivalent for purposes of the reaction. In an alternate procedure, compound VIII may first be N-debenzylated by treatment with a catalyst such as Pd/C in a non-acidic medium such as methanol for example. The product of this reaction may then be treated with hydrogen using substantially the same conditions described above for converting VIII into IV' thereby producing IV'.

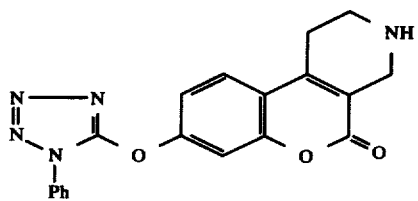

The compounds of the invention display anticholinergic properties when tested by the following procedure:

Conscious guinea pigs, six at a time, are put into a sealed chamber and exposed for 10 minutes to an aerosol of methacholine. Untreated animals or those treated with vehicle will collapse in 1.9±0.1 minutes. Groups of animals are injected intraperitoneally with 25 mg/kg of test compound and exposed in the chamber under the same conditions. Compounds which prolong the collapse time past that of the control animals are considered active. Activity in this procedure indicates that the compound would be of use in treating those bronchospastic diseases such as asthma and bronchitis which have a high degree of cholinergic-mediated vagal tone.

Utilizing the above test procedure, the following results were obtained for representative compounds of the invention.

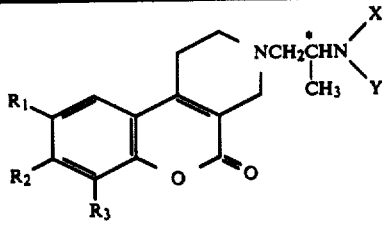

| R₁ | R₂ | R₃ | X | Y | (Minutes Protection) |
|---|---|---|---|---|---|
| Control | | | | | 1.9 to 2.0 |
| H | Me | H | Me | H | 2.1 |
| H | Me | H | Me | Me | 10.0 |
| H | Me | H | Me | Et | 8.8 |
| H | Me | H | Me | n-Pr | 5.4 |
| H | Me | H | Me | n-Bu | 7.8 |
| H | Me | H | Et | H | 10.0 |
| H | Me | H | Et | Et | 6.6 |
| H | Me | H | Et | n-Pr | 7.6 |
| Cl | Me | H | Et | H | 3.1 |
| Cl | Me | H | Et | Et | 3.4 |
| AcNH | Me | H | Me | H | 10.0 |
| Me | Me | H | Me | Me | 4.8 |
| H | H | H | Me | Me | 10.0 |
| H | H | H | Et | Et | 10.0 |
| O—CH₂—O | | H | Me | Me | 2.3 |
| H | CH=CH—CH=CH | | Me | Me | 5.9 |
| H | H | H | Et | H | 10.0 |
| H | H | H | Et | Pr | 6.4 |
| H | MeO | H | Me | H | 8.6 |
| H | MeO | H | Me | Me | 10.0 |
| H | MeO | H | Me | Et | 9.1 |
| H | MeO | H | Me | n-Pr | 10.0 |
| H | MeO | H | Me | n-Bu | 8.6 |
| H | MeO | H | Et | H | 7.5 |
| H | MeO | H | Et | Et | 10.0 |
| H | MeO | H | Et | n-Pr | 10.0 |
| MeO | MeO | H | Me | Me | 5.2 |
| MeO | MeO | H | Me | Et | 6.0 |
| MeO | MeO | H | Me | n-Pr | 2.5 |
| MeO | MeO | H | Et | Et | 7.8 |
| MeO | MeO | H | Et | n-Pr | 3.7 |
| MeO | MeO | H | Et | Bu | 3.7 |
| MeO | MeO | H | Et | s-Bu | 5.4 |
| H | MeO | MeO | Et | H | 9.1 |
| H | MeO | MeO | Me | Et | 5.0 |
| H | MeO | MeO | Et | Et | 7.6 |
| H | MeO | MeO | Me | Me | 5.5 |
| EtO | EtO | H | Me | Me | 7.3 |
| EtO | EtO | H | Et | Et | 10.0 |

In an additional testing procedure, mongrel dogs of either sex, 10.6 to 15.3 kg, are anesthetized with sodium pentobarbital, 30 mg/kg i.v. and then prepared for the monitoring of pulmonary mechanics. A Buxco pulmonary mechanics computer is used to calculate pulmonary resistance, dynamic compliance, and tidal volume from transpulmonary pressure and flow data. Respiratory rate, heart rate and mean arterial blood pressure are also monitored. The femoral vein is cannulated for the delivery of drugs.

Pilocarpine nitrate (0.2 mg/kg/hr) is than infused to induce a bronchospasm and salivary flow. Bunolol (0.5 mg/kg, i.v.) is given 30 minutes prior to the pilocarpine to reduce the protein content, hence, the viscosity of the saliva. Salivary output is collected from a catheterized Wharton's duct at five minute intervals. After salivation has stabilized, 3 control collections are taken at 5 minute intervals followed by a series of cumulative i.v. doses of test compound (1, 3, 10, 30, 100, 300, 1000, 3000, and 10,000 μg/kg) that are injected every 5 minutes for 45 minutes.

The percent inhibition of both the bronchospasm and salivation are calculated for each dose with a return to pre-pilocarpine resistance levels or cessation of salivation equal to a 100% inhibition.

Utilizing this procedure the following results were obtained for representative compounds of the invention.

| R₁ | R₂ | R₃ | X | Y | ID₅₀ μg/kg Bronchospasm | ID₅₀ μg/kg Salivation | Pulmonary Selectivity* |
|---|---|---|---|---|---|---|---|
| H | Me | H | Me | Me | 114 | 421 | 3.7 |
| H | Me | H | Me | Et | 150 | 336 | 2.2 |
| H | Me | H | Et | Et | 111 | 510 | 4.6 |
| H | H | H | Me | Me | 192 | 4147 | 22 |
| H | H | H | Et | Et | 336 | 2310 | 7 |
| H | H | H | Et | H | 210 | 1232 | 6 |
| MeO | MeO | H | Me | Me | 98 | 441 | 4.5 |
| MeO | MeO | H | Et | Et | 73 | 257 | 3.5 |
| EtO | EtO | H | Me | Me | 147 | 303 | 2.1 |

*Pulmonary Selectivity = $\frac{ID_{50} \text{ Salivation}}{ID_{50} \text{ Bronchospasm}}$ where a value >1 indicates the compound is more potent as a bronchodilator than as an antisecretory agent.

The compounds of the invention form pharmaceutically acceptable salts with organic and inorganic acids. Those skilled in the art will recognize that both mono and di salts may be prepared. Examples of suitable acids for salt formation are hydrochloric, sulfuric, phosphoric, acetic, citric, oxalic, malonic, salicylic, malic, fumaric, succinic, ascorbic, maleic, methanesulfonic, and the like. The salts are prepared by contacting the free base form with a sufficient amount of the desired acid to produce either a mono or di salt in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl groups and alkoxy groups contemplated by the invention comprise both straight and branched carbon chains of from 1 to about 6 carbon atoms. Representative of such groups are methyl, ethyl, isopropyl, pentyl, 3-methylpentyl, methoxy, ethoxy, propoxy, 1-ethylbutoxy, pentoxy, and the like.

The term halogen is intended to include fluorine, chlorine, bromine, and iodine.

The compounds of the invention comprise an asymmetric carbon atom which is marked (*) in the structural formula I above. The pure D isomer, pure L isomer, as well as mixtures thereof are contemplated by the invention. Additional asymmetric carbon atoms may be present in a substituent such as an alkyl group. All such isomers as well as mixtures thereof are intended to be included in the invention.

The compounds of the invention can be prepared and administered in a wide variety of oral and parenteral dosage forms. Sprays for both oral and nasal administration are also contemplated. It will be obvious to those skilled in the art that the following dosage forms may comprise as the active component, either a compound of formula I, or a corresponding pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating asthma and bronchitis, the compounds utilized in the pharmaceutical method of this invention are administered at the initial dosage of about 0.5 mg to about 5 mg per kilogram daily. A daily dose range of about 2.0 mg to about 20 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

1,2,3,4-Tetrahydro-5$\underline{H}$-[1,3]benzodioxolo[5',6':5,6-]pyrano[3,4-c]pyridin-5-one hydrochloride A mixture of 3,4-methylenedioxyphenol (125 g, 0.91 moles) and methyl 4-oxo-3-piperidinecarboxylate hydrochloride (125 g, 0.65 moles) is cooled in ice and treated over one hour with 600 ml of 72% sulfuric acid. The mixture is then stirred at room temperature for 64 hours. Ice/water (1.0 kg) is added, followed by conc. ammonium hydroxide, until the pH of the mixture is 9.0. The crude product is filtered, stirred briefly in 2.5% aqueous sodium hydroxide (1.0 l), and refiltered. Several recrystallizations from dilute aqueous hydrochloric acid yielded the product (86.2 g) as the hydrochloride, mp 258°–259° C.

EXAMPLE 2

1,2,3,4-Tetrahydro-7,8-dimethoxy-5$\underline{H}$-[1]benzopyrano[3,4-c]pyridin-5-one hydrochloride Prepared by the method described in Example 1, except that the 2,3-dimethoxyphenol (42.0 g, 0.27 moles) is added in portions to a cooled mixture of the piperidone (30.3 g, 0.15 moles) and 75 ml of conc. sulfuric acid. Recrystallization from methanol with the addition of gaseous hydrogen chloride yielded the product (18.6 g) as the hydrochloride, mp 265°–267° C.

EXAMPLE 3

1,2,3,4-Tetrahydro-8,9,10-trimethoxy-5$\underline{H}$-[1]benzopyrano[3,4-c]pyridin-5-one hydrochloride Prepared by the method described in Example 1 from 3,4,5-trimethoxyphenol (25 g, 0.14 moles) and methyl 4-oxo-3-piperidinecarboxylate hydrochloride (18.8 g, 0.097 moles). Recrystallization from dilute aqueous hydrochloric acid yielded the product (17.5 g) as the hydrochloride, mp 232°–234° C.

EXAMPLE 4

1,2,3,4-Tetrahydro-8,9-dimethyl-5H-[1]benzopyrano[3,4-c]pyridin-5-one

Prepared by the method described in Example 1 from 3,4-dimethylphenol (10.0 g, 0.082 moles) and methyl 4-oxo-3-piperdinecarboxylate hydrochloride (11.3 g, 0.058 moles). Recrystallization from 2-methoxyethanol yielded the product (11.2 g), mp 172°–174° C.

EXAMPLE 5

1,2,3,4-Tetrahydro-12H-naphtho[2',1':5,6]pyrano[3,4-c]pyridin-12-one

Prepared by the method described in Example 1 from 1-napthol (10.0 g, 0.069 moles) and 4-oxo-3-piperidinecarboxylate hydrochloride (9.6 g, 0.05 moles). Recrystallization from 2-propanol/N,N-dimethylformamide yielded the product (3.7 g), mp 227°–230° C.

EXAMPLE 6

1,2,3,4-Tetrahydro-8-(1-methylethyl)-5H-[1]benzopyrano[3,4-c]pyridin-5-one hydrochloride Prepared by the method described in Example 1 from 3-isopropylphenol (150 g, 0.66 moles) and 4-oxo-3-piperidinecarboxylate hydrochloride (114 g, 0.59 moles). Recrystallization from dilute aqueous hydrochloric acid yielded the product (46.6 g) as the hydrochloride, mp 257°–261° C.

EXAMPLE 7

1,2,3,4-Tetrahydro-8,9-dimethoxy-5H-[1]benzopyrano[3,4-c]pyridin-5-one

Prepared by the method described in Example 1 except that the 3,4-dimethoxyphenol (61.5 g, 0.40 moles) is added in one portion to an ice-cooled mixture of ethyl 4-oxo-3-piperidinecarboxylate hydrochloride (75 g, 0.36 moles) and 200 ml of 72% sulfuric acid. Recrystallization from acetonitrile yielded the product (71 g), mp 186°–188° C.

EXAMPLE 8

1,2,3,4-Tetrahydro-8-methoxy-5H-[1]benzopyrano[3,4-c]pyridin-5-one

Prepared by the method described for Example 1 from 3-methoxyphenol (16 g, 0.126 moles) and methyl 4-oxo-3-piperidinecarboxylate hydrochloride (25 g, 0.129 moles). Recrystallization from ethanol gave the product (10.43 g), mp 179°–183° C.

EXAMPLE 9

8-Ethyl-1,2,3,4-tetrahydro-5H-[1]benzopyrano[3,4-c]pyridin-5-one

Prepared by the method described for Example 1 from 3-ethylphenol (12.2 g, 0.1 moles) and methyl 4-oxo-3-piperidinecarboxylate hydrochloride (19.3 g, 0.1 moles). The crude material is washed with water and dried to give the product (6.6 g), mp 80°–85° C.

EXAMPLE 10

8-Phenyl-1,2,3,4-tetrahydro-5H-[1]benzopyrano[3,4-c]pyridin-5-one

Prepared by the method described for Example 1 from 3-phenylphenol (17 g, 0.1 moles) and methyl 4-oxo-3-piperidinecarboxylate hydrochloride (19.3 g, 0.1 moles). The crude material is washed with water and dried to give the product (15 g), mp 250°–270° C.

EXAMPLE 11

8-(1,1-Dimethylethyl)-1,2,3,4-tetrahydro-5H-[1]benzopyrano[3,4-c]pyridin-5-one

Prepared by the method described for Example 1 from 3-t-butylphenol (15 g, 0.1 moles) and methyl 4-oxo-3-piperidinecarboxylate hydrochloride (19.3 g, 0.1 moles). Recrystallization from ethyl acetate gave the product (14.7 g), mp 181°–186° C.

EXAMPLE 12

1,2,3,4-Tetrahydro-8-hydroxy-3-(phenylmethyl)5H-[1]benzopyrano[3,4-c]pyridin-5-one Prepared by the method described for Example 1 from resorcinol (22 g, 0.2 moles) and 1-benzyl-3-carbethoxy-4-piperidone hydrochloride (59.6 g, 0.2 moles). The product (55 g) is converted to 1,2,3,4-tetrahydro-3-(phenylmethyl)-8-[(1-phenyl-1H-tetrazol-5-yl)oxy]-5H-[1]benzopyrano [3,4-c]pyridin-5-one without further purification.

EXAMPLE 13

1,2,3,4-Tetrahydro-8-methyl-5H-[1]benzopyrano[3,4-c]pyridin-5-one

An 80% sulfuric acid solution (80 ml) is stirred and cooled to 5° C. in an ice bath and 3-methylphenol (10.8 ml, 0.10 moles) is added, followed by methyl-4-oxo-3-piperidine carboxylate hydrochloride (20.0 g, 0.10 moles). The mixture is allowed to warm gradually to room temperature. After 48 hours the solution is poured into ice water (400 ml) and stirred until a crystalline precipitate forms. Concentrated ammonium hydroxide is added until the mixture is strongly basic. After one hour the precipitate is filtered off, rinsed with concentrated ammonium hydroxide, then water, and dried. Recrystallization from acetonitrile gave the product (4.5 g), mp 128°–130° C.

EXAMPLE 14

1,2,3,4-Tetrahydro-8-methyl-9-nitro-5H-[1]benzopyrano[3,4-c]pyridin-5-one

A stirred suspension of 1,2,3,4-tetrahydro-8-methyl-5H-[1]benzopyrano[3,4-c]pyridin-5-one (10.0 g, 0.046 moles) in water (10 ml) is cooled in an ice bath. Concentrated sulfuric acid (25 ml) is added, followed after 15 minutes by the dropwise addition of concentrated nitric acid (12 ml). The ice bath is removed and the mixture allowed to warm to room temperature. After 48 hours the mixture is poured over crushed ice, stirred, and made strongly basic by the addition of concentrated ammonium hydroxide. The precipitated product is filtered off, rinsed with water and dried. Recrystallization from acetonitrile gave the product (8.7 g), mp 197°–199° C.

EXAMPLE 15

1,2,3,4-Tetrahydro-8-methoxy-9-nitro-5H-[1]benzopyrano[3,4-c]pyridin-5-one 1,2,3,4-Tetrahydro-8-methoxy-5H-[1]benzopyrano[3,4-c]pyridin-5-one (1.0 g) is dissolved in a mixture of concentrated sulfuric acid (3 ml) and water (2 ml). The resulting solution is cooled in an ice bath and concentrated nitric acid (1 ml) is added. The reaction mixture is stirred at room temperature for 20 hours.

The reaction mixture is poured over ice and made basic with aqueous ammonium hydroxide solution. The product is filtered off and washed with water. Recrystallization from ethanol gave the product (535 mg), mp 200°–205° C. (dec.).

EXAMPLE 16

9-Amino-1,2,3,4-tetrahydro-8-methyl-5H-[1]benzopyrano[3,4-c]pyridin-5-one

A solution of 1,2,3,4-tetrahydro-8-methyl-9-nitro-5H-[1]benzopyrano[3,4-c]pyridin-5-one (6.0 g, 0.023 moles) in N,N-dimethylformamide (100 ml) and methanol (50 ml) is hydrogenated at 50 psi in the presence of Raney Nickel (0.5 g) at room temperature for 20 hours. Additional Raney Nickel (0.5 g) in N,N-dimethylformamide (50 ml) is then added, and hydrogenation resumed until hydrogen uptake ceases. The catalyst is filtered off and rinsed with warm N,N-dimethylformamide. The filtrate is concentrated under reduced pressure and filtered to afford the product (4.3 g), mp 283°–284° C.

EXAMPLE 17

9-Amino-1,2,3,4-tetrahydro-8-methoxy-3-(2-oxopropyl)-5H-[1]benzopyrano[3,4-c]pyridin-5-one 1,2,3,4-Tetrahydro-8-methoxy-9-nitro-5H-[1]benzopyrano[3,4-c]pyridin-5-one (13.0 g) in N,N-dimethylformamide (130 ml) is hydrogenated over Raney Nickel (2 g). The Raney Nickel is filtered off. The solvent is evaporated to give a light brown solid. The solid is triturated with methanol, washed with methanol, and dried to give the product (8.2 g), mp 178°–180° C.

EXAMPLE 18

9-Chloro-1,2,3,4-tetrahydro-8-methyl-5H-[1]benzopyrano[3,4-c]pyridin-5-one

Concentrated hydrochloric acid (8 ml) is added to a stirred suspension of 9-amino-1,2,3,4-tetrahydro-8-methyl-5H-[1]benzopyrano[3,4-c]pyridin-5-one (1.5 g, 0.0065 moles) in water (5 ml). The solution is cooled to −5° C. and a solution of sodium nitrite (0.45 g, 0.0065 moles) in water (4 ml) is added dropwise. After 15 minutes the mixture is added to a solution of freshly prepared cuprous chloride (0.8 g, 0.008 moles) in 20% HCl (8 ml) and stirred for 15 minutes. The suspension is warmed on the steam bath for one hour, allowed to cool, and 10% aqueous potassium carbonate is added until the mixture is basic. The precipitate is filtered off, rinsed with water, dissolved in warm dilute hydrochloric acid, filtered, and reprecipitated by the addition of concentrated ammonium hydroxide. The precipiate is filtered off, rinsed with water, and dried. Recrystallization from ethyl acetate gave the product (0.8 g), mp 184°–185° C.

EXAMPLE 19

1,2,3,4-Tetrahydro-8,9-dimethoxy-3-(2-oxopropyl)-5H-[1]benzopyran[3,4-c]pyridin-5-one A mixture of 1,2,3,4-tetrahydro-8,9-dimethoxy-5H-[1]benzopyrano[3,4-c]pyridin-5-one (26.1 mg, 1.0 mole), 1-chloro-2-propanone (170 g, 1.8 moles), and triethylamine (130 g, 1.3 moles) in 3.5 l of methanol is stirred at reflux for 40 hours. After cooling, the crude product is filtered, stirred briefly in cold water (1.0 l), and refiltered. Recrystallization from methanol/N,N-dimethylformamide yielded the product (228 g), mp 171°–173° C.

EXAMPLE 20

1,2,3,4-Tetrahydro-3-(2-oxopropyl)-5H-[1,3]benzodioxolo[5',6':5,6]pyrano[3,4-c]pyridin-5-one Prepared by the method described in Example 19 from 1,2,3,4-tetrahydro-5H-[1,3]-benzodioxolo[5',6':5,6]pyrano[3,4-c]pyridin-5-one (56.3 g, 0.20 moles). Recrystallization from 2-methoxyethanol/water yielded the product (30 g), mp 167°–170° C.

EXAMPLE 21

1,2,3,4-Tetrahydro-7,8-dimethoxy-3-(2-oxopropyl)-5H-[1]benzopyrano[3,4-c]pyridin-5-one Prepared by the method described in Example 19 from 1,2,3,4-tetrahydro-7,8-dimethoxy-5H-[1]benzopyrano[3,4-c]pyridin-5-one (6.3 g, 0.021 moles). Recrystallization from absolute ethanol yielded the product (4.6 g), mp 145°–147° C.

EXAMPLE 22

1,2,3,4-Tetrahydro-8,9-dimethyl-3-(2-oxopropyl)-5H-[1]benzopyrano[3,4-c]pyridin-5-one A mixture of 1,2,3,4-tetrahydro-8,9-dimethyl-5H-[1]benzopyrano[3,4-c]pyridin-5-one (30 g, 0.13 mole), 1-chloro-2-propanone (23.6 g, 0.25 moles), and triethylamine (27.3 g, 0.27 moles) in 550 ml of absolute ethanol is stirred at reflux for 21 hours. The reaction mixture is evaporated, and the residue is partitioned between dichloromethane (700 ml) and water (500 ml). The two-phase mixture is made basic with conc. ammonium hydroxide, the layers are separated, and the aqueous phase is extracted with fresh dichloromethane. The combined organic layers are backwashed with water, dried over sodium sulfate, and evaporated. Recrystallization of the residue from absolute ethanol yielded the product (23.5 g), mp 136°–138° C.

EXAMPLE 23

1,2,3,4-Tetrahydro-8,9,10-trimethoxy-3-(2-oxopropyl)-5H-[1]benzopyrano[3,4-c]pyridin-5-one Prepared by the method described in Example 22 from 1,2,3,4-tetrahydro-8,9,10-trimethoxy-5H-[1]benzopyrano[3,4-c]pyridin-5-one (10.0 g, 0.031 moles). Recrystallization from ethanol/hexane yielded the product (6.6 g), mp 114°–116° C.

EXAMPLE 24

1,2,3,4-Tetrahydro-8-(1-methylethyl)-3-(2-oxopropyl)-5H-[1]benzopyrano[3,4-c]pyridin-5-one Prepared by the method described in Example 22 from 1,2,3,4-tetrahydro-8-(1-methylethyl)-5H-[1]benzopyrano[3,4-c]pyridin-5-one (28.0 g, 0.097 moles). Recrystallization from 95% ethanol yielded the product (12.4 g), mp 76°–79° C.

EXAMPLE 25

1,2,3,4-Tetrahydro-2-(2-oxopropyl)-12H-naphtho[2',1':5,6]pyrano[3,4-c]pyridin-12-one Prepared by the method described in Example 22 from 1,2,3,4-tetrahydro-12-naphtho[2',1':5,6]pyrano[3,4-c]pyridin-12-one (19.0 g, 0.076 moles). Recrystallization from absolute ethanol yielded the product (11.8 g), mp 142°–145° C.

EXAMPLE 26

1,2,3,4-Tetrahydro-8-methyl-3-(2-oxopropyl)-5H-[1]benzopyrano[3,4-c]pyridin-5-one A mixture of 1,2,3,4-tetrahydro-8-methyl-5H-[1]benzopyrano[3,4-c]pyridin-5-one (2.0 g, 0.009 moles), triethylamine (1.4 ml, 0.010 moles), and 1-chloro-2-propanone (0.8 g, 0.009 moles) in ethanol (50 ml) is stirred and heated to reflux. After 20 hours the mixture is cooled and the precipitate filtered off, rinsed with ethanol, and dried to give the product (1.9 g), mp 128°–129° C.

EXAMPLE 27

1,2,3,4-Tetrahydro-8-methyl-9-nitro-3-(2-oxopropyl)-5H-[1]benzo-pyrano[3,4-c]pyridin-5-one Prepared by the method described for example 26 from 1,2,3,4-tetrahydro-8-methyl-9-nitro-5H-[1]benzopyrano[3,4-c]pyridin-5-one (2.0 g, 0.008 moles), triethylamine (2.3 ml, 0.017 moles), and 1-chloro-2-propanone (0.7 g, 0.008 moles). Recrystallization from methanol gave the product (0.9 g), mp 166°–168° C.

EXAMPLE 28

9-Chloro-1,2,3,4-tetrahydro-8-methyl-3-(2-oxopropyl)-5H-[1]benzo-pyrano[3,4-c]pyridin-5-one Prepared by the method described for example 26 from 9-chloro-1,2,3,4-tetrahydro-8-methyl-5H-[1]benzopyrano[3,4-c]pyridin-5-one (1.6 g, 0.006 moles), triethylamine (1 ml, 0.007 moles) and 1-chloro-2-propanone (0.57 g, 0.006 moles). Recrystallization from isopropanol gave the product (0.5 g), mp 172°–175° C.

EXAMPLE 29

1,2,3,4-Tetrahydro-8-methoxy-3-(2-oxopropyl)-5H-[1]benzopyrano-[3,4-c]pyridin-5-one Prepared by the method described for Example 26 from 1,2,3,4-tetrahydro-8-methoxy-5H-[1]benzopyrano[3,4-c]pyridin-5-one (3.46 g, 0.015 moles) and 1-chloro-2-propanone (2.0 g, 0.022 moles). Recrystallization from methanol gave the product (2.37 g), mp 123°–125° C.

EXAMPLE 30

1,2,3,4-Tetrahydro-8-methoxy-9-nitro-3-(2-oxopropyl)-5H-[1]benzo-pyrano[3,4-c]pyridin-5-one Prepared by the method described for Example 26 from 1,2,3,4-tetrahydro-8-methoxy-9-nitro-5H-[1]benzopyrano[3,4-c]pyridin-5-one (5.52 g, 0.02 moles) and 1-chloro-2-propanone (3.5 g, 0.038 moles). Recrystallization from methanol gave the product (5.7 g), mp 222°–225° C.

EXAMPLE 31

1,2,3,4-Tetrahydro-3-(2-oxopropyl)-5H-[1]benzopyrano[3,4-c]pyridin-5-one.

Prepared by the method described for example 26 from 1,2,3,4-tetrahydro-5H-[1]benzopyrano[3,4-c]pyridin-5-one (5.14 g, 0.025 moles), triethylamine (3.8 g, 0.027 moles), and 1-chloro-2-propanone (2.5 g, 0.027 moles). Recrystallization from ethanol gave the produce (3.8 g) mp 128°–130° C.

EXAMPLE 32

9-Amino-1,2,3,4-tetrahydro-8-methyl-3-(2-oxopropyl)-5H-[1]benzopyrano[3,4-c]pyridin-5-one A solution of 1,2,3,4-tetrahydro-8-methyl-9-nitro-3-(2-oxopropyl)-5H-[1]benzopyrano[3,4-c]pyridin-5-one (17.2 g, 0.054 moles) in N,N-dimethylformamide (300 ml) is hydrogenated at 50 psi at 24° C. in the presence of Raney Nickel until the required amount of hydrogen has been taken up. The catalyst is filtered off and rinsed with hot N,N-dimethylformamide until free of organic material. The filtrate is slightly concentrated and cooled to give the product (10.9 g), mp 196°–198° C.

EXAMPLE 33

9-Amino-1,2,3,4-tetrahydro-8-methoxy-3-(2-oxopropyl)-5H-[1]benzopyrano[3,4-c]pyridin-5-one Prepared by the method described for Example 32 from 1,2,3,4-tetrahydro-8-methoxy-9-nitro-3-(2-oxopropyl)-5H-[1]benzopyrano[3,4-c]pyridin-5-one (13 g). The crude solid is washed with methanol to give the product (8.2 g), mp 178°–180° C.

EXAMPLE 34

N-[1,3,4,5-Tetrahydro-8-methoxy-5-oxo-3-(2-oxopropyl)-2H-[1]benzopyrano[3,4-c]pyridin-9-yl]acetamide 9-Amino-1,2,3,4-tetrahydro-8-methoxy-3-(2-oxopropyl)-5H-[1]benzoprano[3,4-c]pyridin-5-one (5.5 g) is dissolved in water (50 ml) and concentrated hydrochloric acid (4 ml). The solution is heated to 50° C. Acetic anhydride (2.4 ml), sodium acetate (3.0 g) and water (10 ml) are added. The reaction mixture is stirred for 10 minutes, cooled in an ice bath and made basic with ammonium hydroxide solution. The solid is filtered, washed with water and dried to give the product (3.03 g), mp 210°–215° C.

EXAMPLE 35

N-[1,3,4,5-Tetrahydro-8-methyl-5-oxo-3-(2-oxopropyl)-2H-[1]benzopyrano[3,4-c]pyridin-9-yl]-acetamide Prepared by the method described for Example 34 from 9-amino-1,2,3,4-tetrahydro-8-methyl-3-(2-oxopropyl)-5H-[1]benzopyrano[3,4-c]pyridin-5-one (1.4 g 0.005 moles). Basic work-up gave a crystalline precipitate which was filtered off, rinsed with water, and dried. Recrystallization from methanol gave the product (1.1 g), mp 236° C. (dec.).

EXAMPLE 36

1,2,3,4-Tetrahydro-8,9-dihydroxy-3-(2-oxopropyl)-5H-[1]benzopyrano[3,4-c]pyridin-5-one hydrobromide A solution of 1,2,3,4-tetrahydro-8,9-dimethoxy-3-(2-oxopropyl)-5H-[1]benzopyrano[3,4-c]pyridin-5-one (5.0 g, 0.016 moles) in 40 ml of 48% aqueous hydrobromic acid is stirred at reflux for 16 hours. The mixture is cooled, and the precipitated product is filtered and washed several times with cold acetone. The product (5.7 g, mp 280° C. dec.) is used as an intermediate without additional purification.

EXAMPLE 37

1,2,3,4-Tetrahydro-8,9-diethoxy-3-(2-oxopropyl)-5H-[1]benzopyrano[3,4-c]pyridin-5-one A mixture of 1,2,3,4-tetrahydro-8,9-dihydroxy-3-(2-oxopropyl)-5H-[1]benzopyrano[3,4-c]pyridin-5-one hydrobromide (108 g, 0.29 moles), potassium carbonate (155 g, 1.12 moles), and diethyl sulfate (118 g, 0.76 moles) in 2.5 l of acetone is stirred at reflux for 21 hours. Additional diethyl sulfate (59 g, 0.38 moles) is added, and the mixture is heated for an additional 30 hours. The cooled mixture is filtered, and the filter cake is digested twice in hot acetone (500 ml) and refiltered. The combined filtrates are evaporated, and the residue is distributed between dichloromethane (1500 ml) and water (750 ml). The organic layer is separated, washed 4 times with 2.5% aqueous sodium hydroxide (750 ml), dried over sodium sulfate, and evaporated. The residue is recrystallized as the free base from methanol and washed with cold hexane to yield the final product (36.3 g), mp 146°–148° C.

EXAMPLE 38

3-[2-(Dimethylamino)propyl]-1,2,3,4-tetrahydro-8,9-dimethoxy-5H-[1]benzopyrano[3,4-c]pyridin-5-one dihydrochloride A mixture of 1,2,3,4-tetrahydro-8,9-dimethoxy-3-(2-oxopropyl)5H-[1]benzopyrano[3,4-c]pyridin-5-one (72.5 g, 0.23 moles), dimethylamine (112 g, 2.48 moles), and acetic acid (2.5 ml) in 400 ml of methanol is rocked at room temperature for 20 hours. Hydrogenation catalyst (3.8 g of 10% palladium on charcoal) is added, and the mixture is hydrogenated (90° C., 4300 psi) for 6 hours. The catalyst is removed by filtration and the filtrate is evaporated. The residue is dissolved in hot methanol or ethanol, and the solution is treated with excess gaseous hydrogen chloride and filtered hot. After addition of warm diethyl ether to the hot filtrate, cooling yielded the product as the dihydrochloride, which is filtered and washed with cold acetone. A second recrystallization as above yielded the final product (39.1 g), mp 201°–205° C.

EXAMPLE 39

2-[2-(Dimethylamino)propyl]-1,2,3,4-tetrahydro-12H-naphtho-[2',1':5,6]pyrano[3,4-c]pyridin-12-one dihydrochlorine Prepared by the method described in Example 38 from 1,2,3,4-tetrahydro-2-(2-oxopropyl)-12H-naphtho[2',1':5,6]pyrano[3,4-c]pyridin-12-one (8.2 g, 0.027 moles) and dimethylamine (8.0 g, 0.18 moles). Recrystallization from methanol followed by treatment with gaseous hydrogen chloride yielded the product as the dihydrochloride. A second recrystallization from water/dioxane yielded the final product (3.7 g), mp 254°–257° C.

EXAMPLE 40

3-[2-(Dimethylamino)propyl]-1,2,3,4-tetrahydro-7,8-dimethoxy-5H-[1]benzopyrano[3,4-c]pyridin-5-one dihydrochloride Prepared by the method described in Example 38 from 1,2,3,4-tetrahydro-7,8-dimethoxy-3-(2-oxopropyl)-5H-[1]benzopyrano[3,4-c]pyridin-5-one (11.4 g, 0.036 moles) and dimethylamine (12.0 g, 0.27 moles). After conversion to the dihydrochloride salt in methanol, the product is recrystallized from ethanol/N,N-dimethylformamide to yield 2.7 g, mp 193°–197° C.

EXAMPLE 41

3-[2-(Dimethylamino)propyl]-1,2,3,4-tetrahydro-8,9-dimethyl-5H-[1]benzopyrano[3,4-c]pyridin-5-one Prepared by the method described in Example 38 from 1,2,3,4-tetrahydro-8,9-dimethyl-3-(2-oxopropyl)-5H-[1]benzopyrano[3,4-c]pyridin-5-one (7.3 g, 0.026 moles) and dimethylamine (10.0 g, 0.22 moles). Several recrystallizations from acetonitrile yielded the product as the free base (0.7 g) mp 105°–107° C.

EXAMPLE 42

3-[2-(Dimethylamino)propyl]-1,2,3,4-tetrahydro-8,9,10-trimethoxy-5H-[1]benzopyrano[3,4-c]pyridin-5-one dihydrochloride Prepared by the method described in Example 38 from 1,2,3,4-tetrahydro-8,9,10-trimethoxy-3-(2-oxopropyl)-5H-[1]benzopyrano[3,4-c]pyridin-5-one (9.9 g, 0.029 moles) and dimethylamine (1.4 g, 0.030 moles), except that the reaction solvent is 2-methoxyethanol. The residue after catalyst removal and evaporation is partitioned between dichloromethane and dilute aqueous base. After conversion to the dihydrochloride in ethanol, recrystallization from ethanol/N,N-dimethylformamide yielded the final product (0.50 g), mp 218°–224° C.

EXAMPLE 43

3-[2-(Dimethylamino)propyl]-1,2,3,4-tetrahydro-5H-[1,3]benzodioxolo]5',6':5,6]pyrano[3,4-c]pyridin-5-one dihydrochloride Prepared by the method described in Example 38 from 1,2,3,4-tetrahydro-3-(2-oxopropyl)-5H-[1,3]benzodioxolo[5',6':5,6]pyrano[3,4-c]pyridin-5-one (11.6 g, 0.039 moles) and dimethylamine (20 g, 0.44 moles). The product is converted to the dihydrochloride with gaseous hydrogen chloride in methanol. Additional recrystallization from aqueous methanol yielded the final product (2.7 g), mp 236° C. (dec.).

EXAMPLE 44

3-[2-(Dimethylamino)propyl]-1,2,3,4-tetrahydro-8,9-diethoxy-5H-[1]benzopyrano[3,4-c]pyridin-5-one dihydrochloride Prepared by the method described in Example 38 from 1,2,3,4-tetrahydro-8,9-diethoxy-3-(2-oxopropyl)-5H-[1]benzopyrano[3,4-c]pyridin-5-one (35.9 g, 0.10 moles) and dimethylamine (50 g, 1.11 moles). The product is converted to the dihydrochloride with gaseous hydrogen chloride in methanol. An additional recrystallization from methanol/diethyl ether yielded the final product (6.8 g), mp 210° C. (dec.).

EXAMPLE 45

3-[2-(Dimethylamino)propyl]-1,2,3,4-tetrahydro-8-methoxy-5H-[1]benzopyrano[3,4-c]pyridin-5-one dihydrochloride Prepared by the method described for Example 38 from 1,2,3,4-tetrahydro-8-methoxy-3-(2-oxopropyl)-5H-[1]benzopyrano[3,4-c]pyridin-5-one (2.12 g, 0.0074 moles) and dimethylamine (3.0 g, 0.07 moles). Recrystallization from ethanol gave the product (2.05 g), mp 240°–245° C.

EXAMPLE 46

3-[2-(Dimethylamino)propyl]-1,2,3,4-tetrahydro-8-methyl-5H-[1]-benzopyrano[3,4-c]pyridin-5-one Prepared by the method described for Example 38 from 1,2,3,4-tetrahydro-8-methyl-3-(2-oxopropyl)-5H-[1]benzopyrano[3,4-c]pyridin-5-one (2.0 g, 0.007 moles) and dimethylamine (5 g, 0.111 moles). Recrystallization from ethanol gave the product (1.2 g) as the dihydrochloride 10:7 hydrate, mp 224° C. (dec.).

EXAMPLE 47

3-[2-(Dimethylamino)propyl]-1,2,3,4-tetrahydro-5H-[1]benzopyrano[3,4-c]pyridin-5-one Prepared by the method described for Example 38 from 1,2,3,4-tetrahydro-3-(2-oxopropyl)-5H-[1]benzopyrano[3,4-c]pyridin-5-one (3.0 g, 0.012 moles) and dimethylamine (3 g, 0.067 moles). The product was obtained as the dihydrochloride 10:7 hydrate, mp 241° C. (dec.).

EXAMPLE 48

N-[3-(2-Dimethylamino)propyl]-1,3,4,5-tetrahydro-8-methoxy-5-oxo-2H-[1]benzopyrano[3,4-c]pyridin-9-yl acetamide Prepared by the method described for Example 38 from N-[1,3,4,5-tetrahydro-8-methoxy-5-oxo-3-(2-oxopropyl)-2H-[1]benzopyrano[3,4-c]pyridin-9-yl]acetamide (2.7 g, 0.0078 moles) and dimethylamine (3.0 g, 0.067 moles). Recrystallization from ethyl acetate gave the product (1.7 g), mp 168°-172° C.

EXAMPLE 49

3-[2-(Ethylamino)propyl]-1,2,3,4-tetrahydro-8,9-dimethoxy-5H-[1]benzopyrano[3,4-c]pyridin-5-one dihydrochloride A mixture of 1,2,3,4-tetrahydro-8,9-dimethoxy-3-(2-oxopropyl)-5H-benzopyrano[3,4-c]pyridin-5-one (95.3 g, 0.30 moles), ethylamine (26.8 g, 0.60 moles), anhydrous calcium sulfate (65 g, 0.48 moles), and glacial acetic acid (3.0 ml) in 3300 ml of tetrahydrofuran is shaken overnight at 40° in a pressure reactor. The reaction mixture is filtered, and the filtrate is hydrogenated over platinum/charcoal (10.0 g catalyst, 25°, 50 psi) for 48 hours. The catalyst is removed by filtration, and the filtrate is evaporated. The residue is dissolved in hot absolute ethanol, and the solution is treated with excess gaseous hydrogen chloride, filtered hot, and the filtrate is treated with warm diethyl ether. Cooling gave the product as the dihydrochloride salt, which is filtered and washed with cold acetone. A second recrystallization as above yielded the final product (75.5 g) mp 210° C. (dec.).

EXAMPLE 50

3-[2-(Ethylamino)propyl]-1,2,3,4-tetrahydro-7,8-dimethoxy-5H-[1]benzopyrano[3,4-c]pyridin-5-one Prepared by the method described in Example 49 from 1,2,3,4-tetrahydro-7,8-dimethoxy-3-(2-oxopropyl)-5H-benzopyrano[3,4-c]-pyridin-5-one (49.6 g, 0.16 moles) and ethylamine (21.2 g, 0.47 moles). Recrystallization from ethyl acetate/hexane yielded the product (30.7 g) as the free base, mp 125°-127° C.

EXAMPLE 51

3-[2-(Ethylamino)propyl]-1,2,3,4-tetrahydro-5H-[1]benzopyrano[3,4-c]pyridin-5-one A mixture of 1,2,3,4-tetrahydro-3-(2-oxopropyl)-5H-[1]benzopyrano[3,4-c]pyridin-5-one (18.2 g, 0.071 moles), ethylamine (10 ml, 0.153 moles), anhydrous calcium sulfate (15 g), and glacial acetic acid (1 ml) in tetrahydrofuran (450 ml) is shaken at 40° C. in a pressure vessel. After 18 hours the mixture is cooled and filtered. The filtrate is hydrogenated at 25° C. and 50 psi in the presence of 10% platinum or carbon until hydrogen uptake ceases. The catalyst is removed by filtration, and the filtrate is evaporated under reduced pressure. Recrystallization of the residue from ethyl acetate gave the product (10.5 g), mp 104°-105° C.

EXAMPLE 52

9-Chloro-3-[2-(ethylamino)propyl]-1,2,3,4-tetrahydro-8-methyl-5H-[1]benzopyrano[3,4-c]pyridin-5-one Prepared by the method described for example 51 from 9-chloro-1,2,3,4-tetrahydro-8-methyl-3-(2-oxopropyl)-5H-[1]benzopyrano[3,4-c]pyridin-5-one (6.2 g, 0.020 moles) and ethylamine (6 ml, 0.092 moles). Recrystallization from ethyl acetate gave the product (1.4 g), mp 162°-163° C.

EXAMPLE 53

N-[1,3,4,5-Tetrahydro-8-methyl-3-[2-(methylamino)propyl]-5-oxo-2H-[1]benzopyrano[3,4-c]pyridin-9-yl]acetamide Prepared by the method described for Example 51 from N-[1,3,4,5-tetrahydro-8-methyl-5-oxo-3-(2-oxopropyl)-2H-[1]benzopyrano[3,4-c]pyridin-9-yl]acetamide (5.1 g, 0.016 moles) and methylamine (2.2 ml, 0.050 moles). Sufficient methanol is added to effect solution. Recrystallization from ethanol gave the product (3.0 g), mp 187°-188° C.

EXAMPLE 54

3-[2-(Ethylamine)propyl]-1,2,3,4-tetrahydro-8-methyl-5H-[1]benzopyrano[3,4-c]pyridin-5-one Prepared by the method described for Example 51 from 1,2,3,4-tetrahydro-8-methyl-3-(2-oxopropyl)-5H-[1]benzopyrano[3,4-c]pyridin-5-one (20.2 g, 0.074 moles), and ethylamine (12 ml, 0.183 moles). Recrystallization from isopropyl ether/ethyl acetate 4:1 gave the product (18.5 g), mp 120°-121° C.

EXAMPLE 55

1,2,3,4-Tetrahydro-8-methyl-3-[2-(methylamine)propyl]-5H-[1]-benzopyrano[3,4-c]pyridin-5-one Prepared by the method described for example 51 from 1,2,3,4-tetrahydro-8-methyl-3-(2-oxopropyl)-5H-[1]benzopyrano[3,4-c]pyridin-5-one (16.7 g, 0.062 moles) and methylamine (8 ml, 0.18 moles). Recrystallization from ethyl acetate gave the product (15.0 g), mp 123°-125° C.

EXAMPLE 56

3-[2-(Ethylamino)propyl]-1,2,3,4-tetrahydro-8-methoxy-5H-[1]benzopyrano[3,4-c]pyridin-5-one Prepared by the method described for Example 51 from 1,2,3,4-tetrahydro-8-methoxy-3-(2-oxopropyl)-5H-[1]benzopyrano[3,4-c]pyridin-5-one (14.9 g, 0.052 moles) and ethylamine (5 ml, 0.07 moles). Recrystallization from ethyl acetate gave the product (7.1 g), mp 97°–100° C.

EXAMPLE 57

1,2,3,4-Tetrahydro-8-methoxy-3-[2-(methylamino)-propyl]-5H-[1]benzopyrano[3,4-c]pyridin-5-one Prepared by the method described for Example 51 from 1,2,3,4-tetrahydro-8-methoxy-3-(2-oxopropyl)-5H-[1]benzopyrano[3,4-c]pyridin-5-one (16.5 g, 0.057 moles) and methylamine (8 ml, 0.18 moles). Recrystallization from ethyl acetate gave the product (12.0 g), mp 109°–111° C.

EXAMPLE 58

1,2,3,4-Tetrahydro-8,9-dimethoxy-3-[2-(methylamino)-propyl]-5H-[1]benzopyrano[3,4-c]pyridin-5-one Prepared by the method described for Example 51 from 1,2,3,4-tetrahydro-8,9-dimethoxy-3-(2-oxopropyl)-5H-[1]benzopyrano[3,4-c]pyridin-5-one (25.0 g, 0.08 moles) and methylamine (5 g, 0.016 moles). Recrystallization from acetonitrile gave the product (15.5 g), mp 137°–139° C.

EXAMPLE 59

3-[2-(Ethylmethylamino)propyl]-1,2,3,4-tetrahydro-8-methyl-5H-[1]benzopyrano[3,4-c]pyridin-5-one A solution of 1,2,3,4-tetrahydro-8-methyl-3-[2-(methylamino)propyl]-5H-[1]benzopyrano[3,4-c]pyridin-5-one (3.0 g, 0.010 moles) in glacial acetic acid (20 ml) is heated to 55° C. under nitrogen. Sodium borohydride (2.4 g, 0.630 moles) is added portionwise. The mixture is stirred, heated for 20 hours, cooled, diluted with ice water (150 ml), made strongly basic by the addition of concentrated ammonium hydroxide, and extracted with dichloromethane (3×75 ml). The combined extracts are dried over magnesium sulfate and evaporated under reduced pressure. The oily residue is treated with a small amount of diisopropyl ether, filtered, and the filtrate evaporated under reduced pressure. The syrup obtained is dissolved in absolute ethanol, cooled in an ice bath and saturated with HCl gas. After overnight refrigeration the product is filtered off, rinsed with acetone, and sucked dry. Recrystallization from ethanol gave the product (3.0 g) as the dihydrochloride, 20:9 hydrate, mp 245° C. (dec.).

EXAMPLE 60

3-[2-(Diethylamino)propyl]-1,2,3,4-tetrahydro-8-methoxy-5H-[1]benzopyrano[3,4-c]pyridin-5-one Prepared by the method described for Example 59 from 3-[2-(ethylamino)propyl]-1,2,3,4-tetrahydro-8-methoxy-5H-[1]benzopyrano[3,4-c]pyridin-5-one (3.0 g, 0.009 moles), glacial acetic acid (20 ml), and sodium borohydride (2.5 g, 0.066 moles). The free base is obtained crystalline. Recrystallization from isopropyl ether gave the product (1.9 g), mp 83°–85° C.

EXAMPLE 61

3-[2-(Ethylpropylamino)propyl]-1,2,3,4-tetrahydro-8-methoxy-5H-[1]benzopyrano[3,4-c]pyridin-5-one Prepared by the method described for Example 59 from 3-[2-(ethylamino)propyl]-1,2,3,4-tetrahydro-8-methoxy-5H-[1]benzopyrano[3,4-c]pyridin-5-one (3.0 g, 0.009 moles), propionic acid (20 ml), and sodium borohydride (2.0 g, 0.053 moles). The free base is obtained crystalline. Recrystallization from acetonitrile gave the product (2.0 g), mp 100°–101° C.

EXAMPLE 62

3-[2-(Ethylmethylamino)propyl]-1,2,3,4-tetrahydro-8-methoxy-5H-[1]benzopyrano[3,4-c]pyridin-5-one Prepared by the method described for Example 59 from 1,2,3,4-tetrahydro-8-methoxy-3-[2(methylamino)-propyl]-5H-[1]benzopyrano[3,4-c]pyridin-5-one (3.0 g, 0.010 moles), acetic acid (20 ml), and sodium borohydride (2.0 g, 0.053 moles). The product crystallized as the free base. Recrystallization from isopropyl ether gave the product (2.5 g), mp 102°–104° C.

EXAMPLE 63

1,2,3,4-Tetrahydro-8,9-dimethoxy-3-[2-(methylpropylamino)propyl]-5H-[1]benzopyrano[3,4-c]pyridin-5-one Prepared by the method described for Example 59 from 1,2,3,4-tetrahydro-8,9-dimethoxy-3-[2-(methylamino)propyl]-5H-[1]benzopyrano[3,4-c]pyridin-5-one (4.0 g, 0.012 moles), propionic acid (25 ml), and sodium borohydride (2.2 g, 0.057 moles). The product crystallized as the free base. Recrystallization from isopropyl ether gave the product (2.0 g), mp 81°–85° C.

EXAMPLE 64

1,2,3,4-Tetrahydro-8-methoxy-3[2-(methylpropylamino)propyl]-5H-[1]benzopyrano[3,4-c]pyridin-5-one Prepared by the method described for Example 59 from 1,2,3,4-tetrahydro-8-methoxy-3-[2-(methylamino)-propyl]-5H-[1]benzopyrano[3,4-c]pyridin-5-one (3.0 g, 0.010 moles), propionic acid (20 ml), and sodium borohydride (2.0 g, 0.053 moles). During aqueous workup the product precipitates as the free base and is filtered off, rinsed, and dried. Recrystallization from hexane/pentane, 3:2, gave the product (1.9 g), mp 69°–71° C.

EXAMPLE 65

1,2,3,4-Tetrahydro-8-methyl-3-[2-(methylpropylamino)propyl]-5H-[1]benzopyrano[3,4-c]pyridin-5-one Prepared by the method described for Example 59 from 1,2,3,4-tetrahydro-8-methyl-3-[2-(methylamino)-propyl]-5H-[1]benzopyrano[3,4-c]pyridin-5-one (3.0 g, 0.010 moles), propionic acid (20 ml), and sodium borohydride (2.4 g, 0.063 moles). Recrystallization from ethanol gave the product (2.2 g) as the dihydrochloride, 5:1 hydrate, mp 238° C. (dec.).

EXAMPLE 66

3-[2-(Butylmethylamino)propyl)]-1,2,3,4-tetrahydro-8-methoxy-5H-[1]benzopyrano[3,4-c]pyridin-5-one Prepared by the method described for Example 59 from 1,2,3,4-tetrahydro-8-methoxy-3-[2-(methylamino)-propyl]-5H-[1]benzopyrano[3,4-c]pyridin-5-one (3.0 g, 0.010 moles), n-butyric acid (20 ml), and sodium borohydride (2.0 g, 0.053 moles). Recrystallization of the free base from isopropyl ether gave the product (0.9 g), mp 57°–59° C.

EXAMPLE 67

9-Chloro-3-[2-(diethylamino)propyl]-1,2,3,4-tetrahydro-8-methyl-5H-[1]benzopyrano[3,4-c]pyridin-5-one Prepared by the method described for Example 59 from 9-chloro-3-[2-(ethylamino)propyl]-1,2,3,4-tetrahydro-8-methyl-5H-[1]benzopyrano[3,4-c]pyridin-5-one (0.9 g, 0.003 moles), glacial acetic acid (5 ml), and sodium borohydride (0.6 g, 0.016 moles). Recrystallization from isopropyl ether gave the product (0.45 g), mp 78°–80° C.

EXAMPLE 68

3-[2-(Butylmethylamino)propyl]-1,2,3,4-tetrahydro-8-methyl-5H-[1]benzopyrano[3,4-c]pyridin-5-one Prepared by the method described for Example 59 from 1,2,3,4-tetrahydro-8-methyl-3-[2-(methylamino)propyl]-5H-[1]benzopyrano[3,4-c]pyridin-5-one (3.0 g, 0.010 moles, n-butyric acid (20 ml), and sodium borohydride (2.4 g, 0.063 moles). Recrystallization from ethanol gave the product (1.6 g) as the dihydrochloride, 10:7 hydrate, mp 242° C. (dec.).

EXAMPLE 69

3-[2-(Diethylamino)propyl]-1,2,3,4-tetrahydro-8-methyl-5H-[1]benzopyrano[3,4-c]pyridin-5-one Prepared by the method described for Example 59 from 3-[2-(ethylamino)propyl]-1,2,3,4-tetrahydro-8-methyl-5H-[1]benzopyrano[3,4-c]pyridin-5-one (3.0 g, 0.010 moles), glacial acetic acid (20 ml), and sodium borohydride (2.3 g, 0.061 moles). Recrystallization from ethanol gave the product (2.0 g) as the dihydrochloride, mp 254° C. (dec.).

EXAMPLE 70

3-[2-(Ethylpropylamino)propyl]-1,2,3,4-tetrahydro-8-methyl-5H-[1]benzopyrano[3,4-c]pyridin-5-one Prepared by the method described for Example 59 from 3-[2-(ethylamino)propyl]-1,2,3,4-tetrahydro-8-methyl-5H-[1]benzopyrano[3,4-c]pyridin-5-one (3.0 g, 0.010 moles), propionic acid (20 ml), and sodium borohydride (2.3 g, 0.061 moles). Recrystallization from ethanol gave the product (3.0 g) as the dihydrochloride, 5:1 hydrate, mp 248° C. (dec.).

EXAMPLE 71

3-[2-(Diethylamino)propyl]-1,2,3,4-tetrahydro-5H-[1]benzopyrano[3,4-c]pyridin-5-one Prepared by the method described for Example 59 from 3-[2-(ethylamino)propyl]-1,2,3,4-tetrahydro-5H-[1]benzopyrano[3,4-c]pyridin-5-one (3.0 g, 0.010 moles), glacial acetic acid (20 ml), and sodium borohydride (2.4 g, 0.063 moles). The product was obtained as the dihydrochloride, 5:4 hydrate (3.3 g), mp 234° C. (dec.).

EXAMPLE 72

3-[2-(Ethylpropylamino)propyl]-1,2,3,4-tetrahydro-5H-[1]benzopyrano[3,4-c]pyridin-5-one Prepared by the method described for Example 59 from 3-[2-(ethylamino)propyl]-1,2,3,4-tetrahydro-5H-[1]benzopyrano[3,4-c]pyridin-5-one (3.0 g, 0.010 moles), propionic acid (20 ml), and sodium borohydride (2.4 g, 0.063 moles). The product was obtained as the dihydrochloride 5:4 hydrate (1.9 g), mp 238° C. (dec.).

EXAMPLE 73

3-[2-(Diethylamino)propyl]-1,2,3,4-tetrahydro-8,9-dimethoxy-5H-[1]benzopyrano[3,4-c]pyridin-5-one dihydrochloride A mixture of 3-[2-(ethylamino)propyl]-1,2,3,4-tetrahydro-8,9-dimethoxy-5H-[1]benzopyrano[3,4-c]pyridin-5-one dihydrochloride (46.6 g, 0.11 moles), sodium acetate (18.2 g, 0.22 moles), and glacial acetic acid (166 g, 2.77 moles) in tetrahydrofuran (750 ml) is stirred and heated to 50°–55° under a nitrogen atmosphere. Sodium borohydride (22.8 g, 0.60 moles) is added to the mixture over a 3 hour period. After heating for an additional 43 hours, the mixture is cooled in ice, treated cautiously with ice water (1 kg), and condensed to a volume of 1.0 l. The mixture is again cooled in ice and 50% aqueous sodium hydroxide is added until the pH is 11.0. Dichloromethane is used to extract the product, and the combined organic layers are washed with brine, dried over sodium sulfate, and evaporated. The residue is dissolved in hot 95% ethanol, treated with gaseous hydrogen chloride, filtered hot, and the filtrate is treated with diethyl ether. Cooling gives the product as the dihydrochloride salt, which is filtered and washed with cold acetone. A second recrystallization as above yielded the final product (36.0 g), mp 205° C. (dec.).

EXAMPLE 74

3-[2-(Butylethylamino)propyl]-1,2,3,4-tetrahydro-8,9-dimethoxy-5H-[1]benzopyrano[3,4-c]pyridin-5-one Prepared by the method described in Example 73 from 3-[2-(ethylamino)propyl]-1,2,3,4-tetrahydro-8,9-dimethoxy-5H-[1]benzopyrano[3,4-c]pyridin-5-one dihydrochloride (6.7 g, 0.016 moles), sodium acetate (5.2 g, 0.063 moles), sodium borohydride (3.3 g, 0.087 moles), and n-butyric acid (28.9 g, 0.33 moles) instead of acetic acid. Several recrystallizations from diisopropyl ether yielded the final product as the free base (3.0 g), mp 108°–111° C.

EXAMPLE 75

3-[2-(Ethylpropylamino)propyl]-1,2,3,4-tetrahydro-8,9-dimethoxy-5H-[1]benzopyrano[3,4-c]pyridin-5-one Prepared by the method described in Example 73 from 3-[2-(ethylamino)propyl]-1,2,3,4-tetrahydro-8,9-dimethoxy-5H-[1]benzopyrano[3,4-c]pyridin-5-one dihydrochloride (6.7 g, 0.016 moles), sodium acetate (2.6 g, 0.032 moles), sodium borohydride (3.3 g, 0.087 moles), and propionic acid (29.8 g, 0.40 moles) instead of acetic acid. Several recrystallizations from diisopropyl ether yielded the product as the free base (2.4 g), mp 93°–96° C.

EXAMPLE 76

3-[2-(Diethylamino)propyl]-1,2,3,4-tetrahydro-7,8-dimethoxy-5H-[1]benzopyrano[3,4-c]pyridin-5-one Prepared by the method described in Example 73 from 3-[2-(ethylamino)propyl]-1,2,3,4-tetrahydro-7,8-dimethoxy-5H-[1]benzopyrano[3,4-c]pyridin-5-one (10.0 g, 0.029 moles), sodium acetate (4.7 g, 0.058 moles), acetic acid (43.2 g, 0.72 moles), and sodium borohydride (5.9 g, 0.16 moles). Several recrystallizations from ethyl acetate/hexane yielded the product as the free base (2.3 g), mp 99°–100° C.

EXAMPLE 77

3-[2-[Ethyl(2-methylpropyl)amino]propyl]-1,2,3,4-tetrahydro-8,9-dimethoxy-5H-[1]benzopyrano[3,4-c]pyridin-5-one Prepared by the method described in Example 73 from 3-[2-(ethylamino)propyl]-1,2,3,4-tetrahydro-8,9-dimethoxy-5H-[1]benzopyrano[3,4-c]pyridin-5-one dihydrochloride (6.7 g, 0.016 moles), sodium acetate (2.6 g, 0.032 moles), sodium borohydride (3.3 g, 0.087 moles), and 2-methylpropionic acid (28.5 g, 0.32 moles) instead of acetic acid. Several recrystallizations from diisopropyl ether yielded the final product as the free base (1.4 g), mp 108°–111° C.

EXAMPLE 78

3-[2-(Ethylmethylamino)propyl]-1,2,3,4-tetrahydro-8,9-dimethoxy-5H-[1]benzopyrano[3,4-c]pyridin-5-one dihydrochloride A suspension of 3-[2-(ethylamino)propyl]-1,2,3,4-tetrahydro-8,9-dimethoxy-5H-[1]benzopyrano[3,4-c]pyridin-5-one dihydrochloride (6.9 g, 0.017 moles) in methanol (100 ml) is cooled in ice and treated with triethylamine (1.6 g, 0.016 moles) followed by 37% aqueous formaldehyde (6.4 g, 0.21 moles). The ice bath is removed and the mixture is stirred at reflux under nitrogen for 2 hours. The mixture is again cooled in ice while sodium borohydride (2.2 g, 0.058 moles) is added over 30 minutes. After removal of the ice bath, the mixture is again stirred at reflux for 16 hours. The product is then isolated as the dihydrochloride by the method described in Example 73. Several recrystallizations of the dihydrochloride from ethanol/diethyl ether yielded the final product (2.3 g), mp 187° C. (dec.).

EXAMPLE 79

3-[2-(Ethylmethylamino)propyl]-1,2,3,4-tetrahydro-7,8-dimethoxy-5H-[1]benzopyrano[3,4-c]pyridin-5-one dihydrochloride Prepared by the method described in Example 78 from 3-[2-(ethylamino)propyl]-1,2,3,4-tetrahydro-7,8-dimethoxy-5H-[1]benzopyrano[3,4-c]pyridin-5-one (10.0 g, 0.029 moles), except that the addition of the triethylamine is omitted, and instead, a few drops of conc. hydrochloric acid are added before the addition of the formaldehyde solution. After conversion to the dihydrochloride, several recrystallizations from 2-propanol yielded the final product (1.5 g), mp 182°–184° C.

EXAMPLE 80

3-[2-(Diethylamino)propyl]-1,2,3,4-tetrahydro-8,9-dihydroxy-5H-[1]benzopyrano[3,4-c]pyridin-5-one dihydrobromide Prepared by the method described in Example 36 from 3-[2-(diethylamino)propyl]-1,2,3,4-tetrahydro-8,9-dimethoxy-5H-[1]benzopyrano[3,4-c]pyridin-5-one dihydrochloride (23.3 g, 0.052 moles) and 48% aqueous hydrobromic acid (200 ml). After washing several times with cold acetone, the product (25.0 g, mp 257°–258° C.) is used as an intermediate without additional purification.

EXAMPLE 81

3-[2-(Diethylamino)propyl]-1,2,3,4-tetrahydro-8,9-diethoxy-5H-[1]benzopyrano[3,4-c]pyridin-5-one dihydrochloride Prepared by the method described in Example 37 from 3-[2-(diethylamino)propyl]-1,2,3,4-tetrahydro-8,9-dihydroxy-5H-[1]benzopyrano[3,4-c]pyridin-5-one dihydrobromide (17.0 g, 0.034 moles), potassium carbonate (27.6 g, 0.20 moles), and diethyl sulfate (20.0 g, 0.13 moles). The crude free base product is converted to the dihydrochloride in absolute ethanol. A second recrystallization from ethanol yielded the final product (1.8 g), mp 148°–152° C.

EXAMPLE 82

1,2,3,4-Tetrahydro-3-(phenylmethyl)-8-[(1-phenyl-1H-tetrazol-5-yl)oxy]-5H-[1]benzopyrano[3,4-c]pyridin-5-one A mixture of 1,2,3,4-tetrahydro-8-hydroxy-3(phenylmethyl)-5H-[1]benzopyrano[3,4-c]pyridin-5-one (15 g, 0.049 moles), 5-chloro-1-phenyl-1H-tetrazole (9 g, 0.0498 moles), and potassium carbonate (30 g) in dimethylformamide (250 ml) is heated at 85°–95° C. for 5 hours. The reaction mixture is cooled and poured over ice water. The aqueous mixture is allowed to stand at room temperature overnight. The solid is filtered off and washed with water. Recrystallization from ethyl acetate gave the product (10.14 g), mp 165°–166° C.

EXAMPLE 83

1,2,3,4-Tetrahydro-5H-[1]benzopyrano[3,4-c]pyridin-5-one

A solution of 1,2,3,4-tetrahydro-3-(phenylmethyl)-8-[(1-phenyl-1H-tetrazol-5-yl)oxy]-5H-[1]benzopyrano[3,4-c]pyridin-5-one (21.3 g, 0.047 moles) in acetic acid (210 ml) is hydrogenated at room temperature and 50 psi in the presence of 20% palladium on carbon until hydrogen uptake ceases. The catalyst is removed by filtration and the filtrate evaporated under reduced pressure. The residue is dissolved in water (300 ml) and made strongly basic by the additon of concentrated ammonium hydroxide. The precipitate is filtered off, rinsed with water, and dried. Recrystallization from ethyl acetate gave the product (6.1 g), mp 125°–128° C.

We claim:

1. A compound having the structural formula I

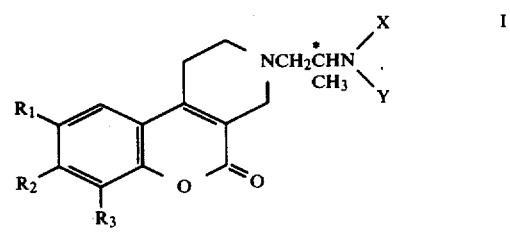

wherein
- $R_1$ is H, alkyl of from 1 to 6 carbon atoms, alkoxy of from 1 to 6 carbon atoms, halo, or acetylamino;
- $R_2$ is H, alkyl of from 1 to 6 carbon atoms, or alkoxy of from 1 to 6 carbon atoms;
- $R_3$ is H, or alkoxy of from 1 to 6 carbon atoms;
- $R_1$ and $R_2$ taken together are $OCH_2O$;
- $R_2$ and $R_3$ taken together are $CH=CH-CH=CH$;
- X is $CH_3$, $C_2H_5$, n-$C_3H_7$, or n-$C_4H_9$;

Y is H, CH$_3$, C$_2$H$_5$ n-C$_3$H$_7$, n-C$_4$H$_9$, or s-C$_4$H$_9$; and the pharmaceutically acceptable salts thereof, provided that R$_1$ and R$_2$ are not both OCH$_3$ when Y is H.

2. A compound defined in claim 1 wherein R$_3$ is H, and the pharmaceutically acceptable salts thereof.

3. A compound defined in claim 1 wherein R$_3$ is H and X is CH$_3$ or C$_2$H$_5$, and the pharmaceutically acceptable salts thereof.

4. The compound defined in claim 1 having the name 3-[2-(dimethylamino)propyl]-1,2,3,4-tetrahydro-8,9-dimethoxy-5H-[1]benzopyrano[3,4-c]pyridin-5-one and the pharmaceutically acceptable salts thereof.

5. The compound defined in claim 1 having the name 3-[2-(ethylamino)propyl]-1,2,3,4-tetrahydro-5H-[1]benzopyrano[3,4-c]pyridin-5-one and the pharmaceutically acceptable salts thereof.

6. The compound of claim 1 having the name 3-[2-(dimethylamino)propyl]-1,2,3,4-tetrahydro-8,9-diethoxy-5H-[1]benzopyrano[3,4-c]pyridin-5-one and the pharmaceutically acceptable salts thereof.

7. The compound defined in claim 1 having the name 3-[2-(dimethylamino)propyl]-1,2,3,4-tetrahydro-8-methyl-5H-[1]benzopyrano[3,4-c]pyridin-5-one and the pharmaceutically acceptable salts thereof.

8. The compound defined in claim 1 having the name 3-[2-(dimethylamino)propyl]-1,2,3,4-tetrahydro-5H-[1]benzopyrano[3,4-c]pyridin-5-one and the pharmaceutically acceptable salts thereof.

9. The compound defined in claim 1 having the name 3-[2-(ethylamino)propyl]-1,2,3,4-tetrahydro-8-methoxy-5H-[1]benzopyrano[3,4-c]pyridin-5-one and the pharmaceutically acceptable salts thereof.

10. The compound defined in claim 1 having the name 3-[2-(ethylmethylamino)propyl]-1,2,3,4-tetrahydro-8-methyl-5H-[1]benzopyrano[3,4-c]pyridin-5-one and the pharmaceutically acceptable salts thereof.

11. The compound defined in claim 1 having the name 3-[2-(diethylamino)propyl]-1,2,3,4-tetrahydro-8-methyl-5H-[1]benzopyrano[3,4-c]pyridin-5-one and the pharmaceutically acceptable salts thereof.

12. The compound defined in claim 1 having the name 3-[2-(diethylamino)propyl]-1,2,3,4-tetrahydro-5H-[1]benzopyrano[3,4-c]pyridin-5-one and the pharmaceutically acceptable salts thereof.

13. The compound defined in claim 1 having the name 3-[2-(diethylamino)propyl]-1,2,3,4-tetrahydro-8,9-dimethoxy-5H-[1]benzopyrano[3,4-c]pyridin-5-one and the pharmaceutically acceptable salts thereof.

14. A pharmaceutical composition consisting essentially of an anti-asthmatically or antibronchitically effective amount of a compound defined in claim 1 in combination with a pharmaceutically acceptable carrier.

15. A method for treating asthma or bronchitis in a mammal in need of such treatment which comprises administering an effective amount of the pharmaceutically composition defined in claim 14 to said mammal.

* * * * *